United States Patent
Lim et al.

(10) Patent No.: US 11,135,073 B2
(45) Date of Patent: Oct. 5, 2021

(54) GAIT ASSISTANCE APPARATUS AND OPERATING METHOD THEREOF

(71) Applicant: Samsung Electronics Co., Ltd., Suwon-si (KR)

(72) Inventors: Bokman Lim, Yongin-si (KR); Kyung-Rock Kim, Yongin-si (KR); Youngbo Shim, Seoul (KR); Jun-Won Jang, Seoul (KR); Seungyong Hyung, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 131 days.

(21) Appl. No.: 15/439,075

(22) Filed: Feb. 22, 2017

(65) Prior Publication Data

US 2018/0116827 A1    May 3, 2018

(30) Foreign Application Priority Data

Oct. 31, 2016    (KR) .................. 10-2016-0143626

(51) Int. Cl.
*A61H 3/00* (2006.01)
*A61F 2/70* (2006.01)
(Continued)

(52) U.S. Cl.
CPC ................ *A61F 2/70* (2013.01); *A61B 5/112* (2013.01); *A61H 3/00* (2013.01); *A63B 21/4009* (2015.10); *A63B 21/4011* (2015.10); *A63B 23/0405* (2013.01); *A63B 24/0006* (2013.01); *A63B 24/0087* (2013.01); *A61B 2505/09* (2013.01); *A61B 2562/0219* (2013.01); *A61B 2562/0247* (2013.01); *A61B 2562/0252* (2013.01);
(Continued)

(58) Field of Classification Search
CPC .................................................... A61H 3/00
See application file for complete search history.

(56) References Cited

U.S. PATENT DOCUMENTS 8,801,641 B2 * 8/2014 Kazerooni ............. A61H 3/008
128/898
9,119,762 B2    9/2015 Endo et al.
(Continued)

FOREIGN PATENT DOCUMENTS

JP    2013/090652 A    5/2013
JP    2013/158346 A    8/2013
(Continued)

OTHER PUBLICATIONS

Hiroaki Kawamoto et al., "Development of Single Leg Version of HAL for Hemiplegia", Annual International Conference of the IEEE, Engineering in Medicine and Biology Society, 2009.

*Primary Examiner* — Jacqueline Wozncki
(74) *Attorney, Agent, or Firm* — Harness, Dickey & Pierce, P.L.C.

(57) ABSTRACT

A gait assistance apparatus including at least one sensor configured to sense a step motion of a user, and an operator configured to determine assistance forces of a right step and a left step of the user based on step motion information of the user and adjust the assistance force for at least one of the right step or the left step of the user based on a result of proportionally adding together the assistance forces of the right step and the left step based on a variable ratio may be provided.

12 Claims, 9 Drawing Sheets

(51) Int. Cl.
*A63B 21/00* (2006.01)
*A61B 5/11* (2006.01)
*A63B 23/04* (2006.01)
*A63B 24/00* (2006.01)
*A61F 2/68* (2006.01)

(52) U.S. Cl.
CPC .......................... *A61B 2562/0261* (2013.01); *A61H 2003/007* (2013.01); *A61H 2201/165* (2013.01); *A61H 2201/1652* (2013.01); *A61H 2201/50* (2013.01); *A61H 2201/5069* (2013.01); *A61H 2201/5079* (2013.01); *A63B 2024/0009* (2013.01)

(56) References Cited

U.S. PATENT DOCUMENTS

| | | | |
|---|---|---|---|
| 9,216,131 | B2 | 12/2015 | Nakashima et al. |
| 9,974,478 | B1* | 5/2018 | Brokaw ................. A61B 5/486 |
| 2003/0093021 | A1* | 5/2003 | Goffer ................... A61F 5/0102 |
| | | | 602/23 |
| 2006/0211956 | A1* | 9/2006 | Sankai ............... A61B 5/04888 |
| | | | 601/5 |
| 2008/0249438 | A1* | 10/2008 | Agrawal ............... A61H 1/0237 |
| | | | 601/35 |
| 2014/0058299 | A1* | 2/2014 | Sankai ................... A61B 5/112 |
| | | | 601/35 |
| 2015/0022362 | A1 | 1/2015 | Lucas et al. |
| 2015/0127018 | A1 | 5/2015 | Lim et al. |
| 2015/0150747 | A1 | 6/2015 | Sankai |
| 2015/0190923 | A1* | 7/2015 | Seo ........................ B25J 9/0006 |
| | | | 602/16 |
| 2015/0374513 | A1* | 12/2015 | Ikeuchi ................. A61F 5/0102 |
| | | | 623/24 |
| 2016/0101515 | A1* | 4/2016 | Lim ......................... A61H 3/00 |
| | | | 623/24 |
| 2018/0220937 | A1* | 8/2018 | Mizuochi .............. A61B 5/1112 |
| 2018/0235831 | A1* | 8/2018 | Jang ........................ A61H 3/00 |
| 2020/0039061 | A1* | 2/2020 | Sankai .................... A61H 3/00 |

FOREIGN PATENT DOCUMENTS

| | | |
|---|---|---|
| JP | 2014/068869 A | 4/2014 |
| JP | 5569885 B2 | 8/2014 |
| KR | 10-1430867 B1 | 8/2014 |
| KR | 10-1476889 B1 | 12/2014 |
| KR | 10-1611042 B1 | 4/2016 |

* cited by examiner

GAIT ASSISTANCE APPARATUS AND OPERATING METHOD THEREOF

CROSS-REFERENCE TO RELATED APPLICATION

This application claims under 35 U.S.C. § 119 to Korean Patent Application No. 10-2016-0143626, filed on Oct. 31, 2016, in the Korean Intellectual Property Office, the entire contents of which are incorporated herein by reference in their entirety.

BACKGROUND

1. Field

At least one example embodiment relates to a gait assistance apparatus and/or an operating method of the gait assistance apparatus. For example, at least some example embodiments relate to a gait assistance apparatus and/or an operating method of the gait assistance apparatus for adjusting an assistance force based on a result of proportionally adding together assistance forces of both steps based on a variable ratio.

2. Description of the Related Art

A wearable gait assistance apparatus may be worn as an external skeleton on a body and may enhance a gait by providing an assistance force to add to muscular strength during walking. A gait assistance apparatus may assist rehabilitation and correction of gaits, and enhance gaits of pedestrians with abnormal gaits such that it is possible for them to walk independently.

A general method of providing an asymmetric assistance force to correct an asymmetric gait of a user and allow a symmetric gait exists. However, the general method may cause a problem of stability or inconvenience for a user because an abnormal leg may be assisted similar to a normal leg without considering a current gait style of a user.

Thus, variable gait assistance for gradually increasing an assistance force for a gait assistance apparatus and an external assistance force for rehabilitation and correction of a gait of a user may be needed.

SUMMARY

Some example embodiments relate to a method of operating a gait assistance apparatus.

In some example embodiments, the method includes determining an assistance force associated with a right step and an assistance force associated with a left step of the gait assistance apparatus based on step motion information of a user; and adjusting at least one of the assistance force associated with the right step and the assistance force associated with the left step based on a result of proportionally adding the assistance force associated with the right step and the assistance force associated with the left step based on a variable ratio.

In some example embodiments, the method further includes receiving the variable ratio from an input device, the input device configured to manually adjust the variable ratio.

In some example embodiments, the method further includes determining the variable ratio based on the step motion information of the user.

In some example embodiments, the determining the variable ratio includes determining a gait variability of the user based on the step motion information of the user; and determining the variable ratio based on the gait variability.

In some example embodiments, the determining of the gait variability includes identifying a gait cycle based on the step motion information of the user; and determining the gait variability based on a similarity between the step motion information obtained during a current interval and the step motion information obtained during a prior interval, the prior interval occurring prior to the current interval.

In some example embodiments, the determining the assistance force associated with the right step includes determining the assistance force to swing a right leg of the user while a left leg of the user acts as a pivot, and the determining the assistance force associated with the left step includes determining the assistance force to swing the left leg while the right leg acts as the pivot.

In some example embodiments, the assistance force associated with the right step includes an assistance force to apply to a right leg of the user during the right step and an assistance force to apply to a left leg of the user during the right step, and the assistance force associated with the left step includes an assistance force to apply to the right leg during the left step and an assistance force to apply to the left leg during the left step.

Some other example embodiments relate to a method of operating a gait assistance apparatus.

In some example embodiments, the method includes determining an assistance force to apply to a right leg and a left leg of a user during a first step of the user and a second step of the user based on step motion information of the user, the second step being subsequent to the first step; and determining an assistance force to apply to the right leg and the left leg during a third step of the user based on a result of proportionally adding the assistance force of the first step and the assistance force of the second step based on a variable ratio, the third step being subsequent to the second step.

In some example embodiments, the method further includes receiving the variable ratio from an input device, the input device configured to manually adjust the variable ratio.

In some example embodiments, the method further includes determining the variable ratio based on the step motion information of the user.

In some example embodiments, the determining of the variable ratio includes determining a gait variability of the user based on the step motion information of the user; and determining the variable ratio based on the gait variability.

Some example embodiments relate to a non-transitory computer-readable storage medium storing a program for causing a processor to perform the method of operating the gait assistance apparatus.

Some example embodiments relate to a gait assistance apparatus.

In some example embodiments, the gait assistance apparatus includes at least one sensor configured to sense a step motion of a user; and a processor configured to, determine an assistance force associated with a right step and an assistance force associated with a left step of the user based on step motion information of the user, and adjust at least one of the assistance force associated with the right step and the assistance force associated with the left step based on a result of proportionally adding the assistance force associated with the right step and the assistance force associated with the left step based on a variable ratio.

In some example embodiments, the apparatus further includes an input device configured to manually adjust the variable ratio.

In some example embodiments, the processor is configured to, determine a gait variability of the user based on the step motion information of the user, and determine the variable ratio based on the gait variability.

In some example embodiments, the processor is configured to, identify a gait cycle based on the step motion information of the user, and determine the gait variability based on a similarity between the step motion information obtained during a current interval and the step motion information obtained during a prior interval, the prior interval occurring prior to the current interval.

In some example embodiments, the apparatus further includes an assistance force transmitter configured to transmit the assistance force associated with the right step and the assistance force associated with the left step to legs of the user.

Additional aspects of example embodiments will be set forth in part in the description which follows and, in part, will be apparent from the description, or may be learned by practice of the disclosure.

BRIEF DESCRIPTION OF THE DRAWINGS

These and/or other aspects will become apparent and more readily appreciated from the following description of example embodiments, taken in conjunction with the accompanying drawings of which.

DETAILED DESCRIPTION

Hereinafter, some example embodiments will be described in detail with reference to the accompanying drawings. Regarding the reference numerals assigned to the elements in the drawings, it should be noted that the same elements will be designated by the same reference numerals, wherever possible, even though they are shown in different drawings. Also, in the description of example embodiments, detailed description of well-known related structures or functions will be omitted when it is deemed that such description will cause ambiguous interpretation of the present disclosure.

It should be understood, however, that there is no intent to limit this disclosure to the particular example embodiments disclosed. On the contrary, example embodiments are to cover all modifications, equivalents, and alternatives falling within the scope of the example embodiments. Like numbers refer to like elements throughout the description of the figures.

In addition, terms such as first, second, A, B, (a), (b), and the like may be used herein to describe components. Each of these terminologies is not used to define an essence, order or sequence of a corresponding component but used merely to distinguish the corresponding component from other component(s). It should be noted that if it is described in the specification that one component is "connected", "coupled", or "joined" to another component, a third component may be "connected", "coupled", and "joined" between the first and second components, although the first component may be directly connected, coupled or joined to the second component.

The terminology used herein is for the purpose of describing particular embodiments only and is not intended to be limiting. As used herein, the singular forms "a," "an," and "the," are intended to include the plural forms as well, unless the context clearly indicates otherwise. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Various example embodiments will now be described more fully with reference to the accompanying drawings in which some example embodiments are shown. In the drawings, the thicknesses of layers and regions are exaggerated for clarity.

Figure 1:
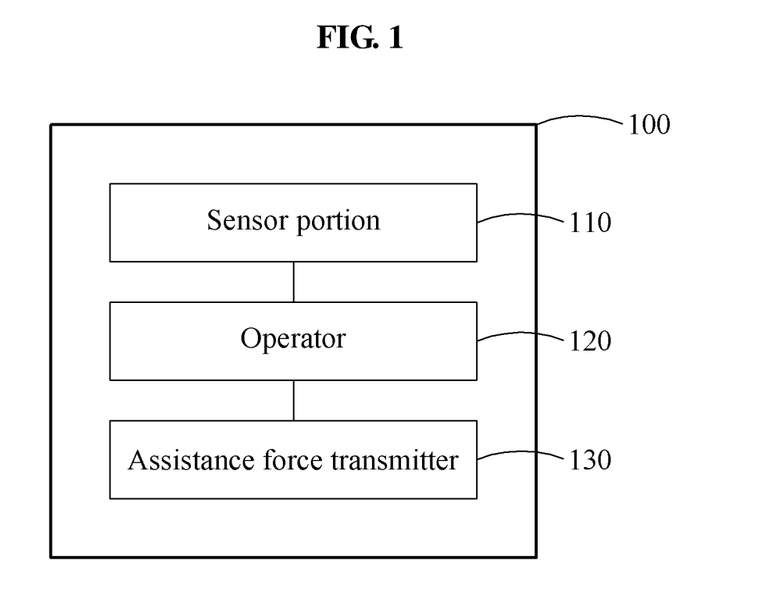
FIG. 1 is a block diagram illustrating a gait assistance apparatus according to some example embodiments.

FIG. 1 is a block diagram illustrating a gait assistance apparatus 100 according to some example embodiments.

Referring to FIG. 1, the gait assistance apparatus 100 may include a sensor portion 110, an operator 120, and an assistance force transmitter 130. The gait assistance apparatus 100 may further include an input device.

The sensor portion 110 may sense step motion information of a user using at least one sensor. For example, the step motion information of the user may include a joint angle and a joint angular velocity associated with a step of the user. In more detail, the step motion information of the user may include a hip joint angle and a hip joint angular velocity of the user.

The sensor portion 110 may include at least one of an encoder sensor and an inertial measurement unit (IMU) sensor. A type of a sensor and a portion to be sensed are not limited to those described in relation to example embodiments, and the type of the sensor and the portion to be sensed may be varied as needed.

The operator 120 may be any processing circuitry such as, but not limited to, a processor, Central Processing Unit (CPU), a controller, an arithmetic logic unit (ALU), a digital signal processor, a microcomputer, a field programmable gate array (FPGA), an Application Specific Integrated Circuit (ASIC), a System-on-Chip (SoC), a programmable logic unit, a microprocessor, or any other device capable of performing operations in a defined manner.

According to one or more example embodiments, the processing circuitry may be described herein as including various functional units that perform various operations and/or functions to increase the clarity of the description. However, in one or more example embodiments, the various operations and/or functions of the functional units may be performed by other ones of the functional units. Further, the processing circuitry may perform the operations and/or functions of the various functional units without sub-dividing the operations and/or functions into these various functional units.

The operator 120 may be included in a frame of the gait assistance apparatus 100 and provided in a personal computer (PC), for example, a desktop computer and a laptop computer, a mobile user equipment, or a server via a wired or wireless connection. A function of the proposed operator 120 is not limited by a form in which it is implemented.

Further, the gait assistance apparatus 100 may include a memory (not shown). The memory may include a nonvolatile memory device, a volatile memory device, a non-transitory storage medium, or a combination of two or more of the above-mentioned devices. For example, the memory may include one or more of a Read Only Memory (ROM), Random Access Memory (RAM), Compact Disk-Read Only Memories (CD-ROMs), magnetic tapes, floppy disks, and an optical recording medium.

The processing circuitry may be configured, through a layout design and/or execution of computer readable instructions stored in the memory, as a special purpose computer to determine assistance forces of a right step and/or a left step of the user based on the step motion information measured by the sensor portion 110. The right step indicates a step that involves a right leg swinging while a left leg acts as a pivot, and the left step indicates a step that involves the left leg swinging while the right leg acts as the pivot. In addition, the assistance force for the right step also refers to an assistance force to be applied to the right leg during the right step in addition to an assistance force to be applied to the left leg during the right step.

Generally, the assistance force for the right step is determined based on motion information of the right step, and the assistance force for the left step is determined based on motion information of the left step. To gradually support an asymmetric gait, the gait assistance apparatus 100 may use an assistance force determined based on motion information of identical steps and an assistance force determined based on motion information of opposite steps when an assistance force for any one step is determined.

For example, when determining the assistance force for the right step, the assistance force determined based on the motion information of the right step and the assistance force determined based on the motion information of the left step may be reflected at a ratio of $1-\alpha r:\alpha r$. When determining the assistance force for the left step, the assistance force determined based on the motion information of the left step and the assistance force determined based on the motion information of the right step may be reflected at a ratio of $1-\alpha l:\alpha l$.

Thus, the method of adjusting the assistance force based on the result of proportionally adding together the assistance force for the right step and the assistance force for the left step may allow a gait of a user to be corrected or rehabilitated by enabling a motion of an opposite leg to reflect a motion of a normal ambulatory leg at a desired (or, alternatively, a predetermined) ratio when the gait of the user is asymmetric due to cerebral apoplexy or neuropathy.

In an example, variable ratios $\alpha r$ and $\alpha l$ at which assistance forces are reflected to both steps are variable values rather than fixed values. For example, each of the variable ratios $\alpha r$ and $\alpha l$ may be set to zero reflecting a natural gait style of a user when a gait assistance apparatus is initially used. In this example, because an assistance force for an opposite step is not reflected, the left step and the right step are individually assisted based on the natural gait style of the user.

Based on a verification that the user is adjusted to the gait assistance apparatus, each of the variable ratios $\alpha r$ and $\alpha l$ may increase to be greater than zero such that the motion of the opposite leg reflects the motion of the normal ambulatory leg at the desired (or, alternatively, the predetermined) ratio. The higher the variable ratios $\alpha r$ and $\alpha l$, the more the motion of the opposite leg reflects the assistance force provided for a leg by the gait assistance apparatus.

An input device that is manually controlled by a user or an assistant, for example, a physical therapist, may change a variable ratio. The input device may include various appropriate devices, for example, a switch, a knob, and a jog dial, configured to adjust the variable ratio. The input device may be replaced with an external remote control or a smart device and may not need to be included in the gait assistance apparatus.

The operator 120 may automatically adjust the variable ratio based on a desired (or, alternatively, a predetermined) reference. For example, the operator 120 may determine a gait variability of the user based on the step motion information of the user. Here, the gait variability may be a parameter indicating a degree of consistency of a gait cycle of a user obtained by analyzing the gait cycle.

The gait assistance apparatus 100 may define and recognize the gait cycle of the user using a finite state machine (FSM) including a plurality of gait states. For example, in a case of a general gait pattern, a gait cycle of a user includes a right step that involves a right leg swinging while a left leg acts as a pivot and a left step that involves the left leg swinging while the right leg acts as the pivot. Detailed description on recognition of the gait cycle using the FSM is provided below.

The operator 120 identifies the gait cycle based on the step motion information of the user and verifies a similarity between step motion information obtained during a recent gait cycle and step motion information obtained during a previous gait cycle by analyzing and comparing the step motion information obtained during the recent gait cycle and the step motion information obtained during the previous gait cycle. The gait assistance apparatus 100 may use one or more of a step time, a joint motion range, a stride, a gait speed, and a bilateral symmetry as references for verifying the similarity. Based on the verification of the similarity between the recent gait cycle and the previous gait cycle, the gait assistance apparatus 100 may verify a degree to which the user is adjusted to the gait assistance apparatus. The gait assistance apparatus 100 may set a value of the gait variability to a relatively low value based on a verification that the user is sufficiently adjusted to a currently provided assistance force in response to the similarity between the step motion information obtained during the recent gait cycle and the step motion information obtained during the previous gait cycle being relatively high.

In response to the gait variability being less than the desired (or, alternatively, the predetermined) reference, the user may not experience discomfort or be placed in a dangerous situation even though an assistance force is adjusted to correct the gait style. Thus, in response to the gait variability being less than the desired (or, alternatively, the predetermined) reference, the operator 120 may correct or rehabilitate the gait of the user by increasing the variable ratios αr and αl.

The gait assistance apparatus 100 may perform a process for adjusting the variable ratios to reflect the gait variability gradually by verifying several times the degree to which the user is adjusted to the gait assistance apparatus. In an example, the gait assistance apparatus 100 adjusts the variable ratio in real time by verifying the degree to which the user is adjusted to the gait assistance apparatus 100. In another example, the gait assistance apparatus 100 records information related to a long-term rehabilitation process, and gradually adjusts the variable ratio by verifying the degree to which the user is adjusted to the gait assistance apparatus 100 based on the recorded information, for example, over days, weeks or months.

The assistance force transmitter 130 may be worn on a leg of the user to provide an assistance force that pushes and pulls the leg. For example, the assistance force applied by the assistance force transmitter 130 may include an assistance torque to be applied to each leg.

Figure 2:
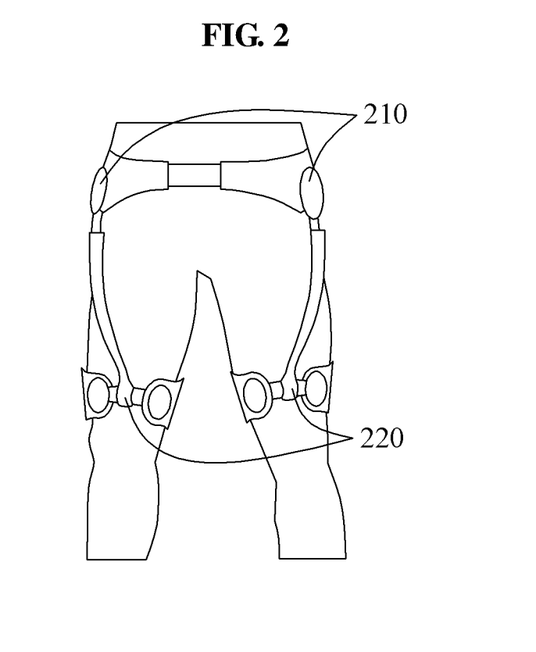
FIGS. 2 through 4 are diagrams illustrating examples of implementations of a gait assistance apparatus according to some example embodiments.

FIG. 2 is a diagram illustrating an example of an implementation of a gait assistance apparatus according to some example embodiments.

Referring to FIG. 2, in the gait assistance apparatus 100, the sensor portion 110 may be embodied as a sensor portion 210 and the assistance force transmitter 130 may be embodied as an assistance force transmitter 220 in some example embodiments.

The sensor portion 210 may sense a progress of a hip joint angle and/or a hip joint angular velocity of a user using at least one of an encoder sensor and/or an inertial measurement unit (IMU) sensor. The sensor portion 210 is configured to transmit step motion information of the user sensed by the sensor portion 210 to the operator 120, where the operator 120 is configured to determine the assistance force based on the step motion information. For example, the sensor portion 210 may transmit the assistance force to a calculator (not shown), for example, a calculating unit included in the operator 120, for determining an assistance force.

The assistance force transmitter 220 may be tightly worn on a thigh above a knee of the user providing an assistance torque that pushes and/or pulls a leg of the user. Although FIG. 2 illustrates that the assistance force transmitter 220 provides the assistance torque to the thigh of the user, example embodiments are not limited thereto. The assistance force transmitter 220 may also support an entire lower body or a portion of the lower body.

Figure 3:
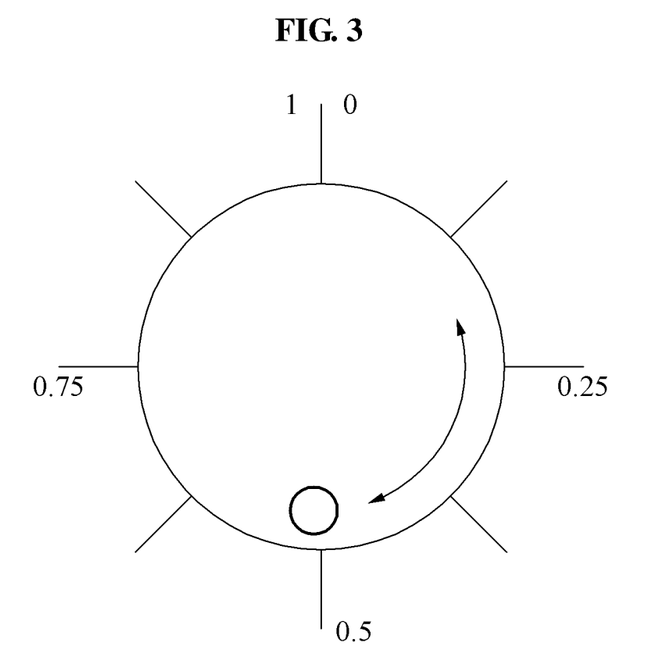
Figure 4:
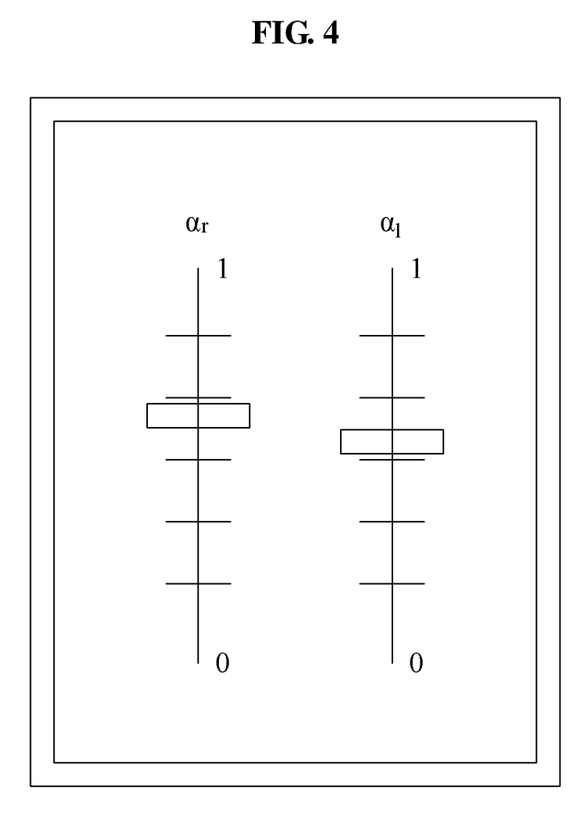

FIGS. 3 and 4 each illustrate an input device of a gait assistance apparatus according to some example embodiments.

Referring to FIGS. 3 and 4, as examples, FIG. 3 illustrates the input device in a form of a jog dial, and FIG. 4 illustrates the input device in a form of a fader. A user or an assistant, for example, a physical therapist, may manually adjust a variable ratio using the input device.

For example, in response to the user experiencing discomfort with a currently provided assistance force while the user is using the gait assistance apparatus 100, an operation of decreasing the variable ratio is performed through the input device. In addition, the assistant, for example, the physical therapist, may perform an operation of increasing the variable ratio through the input device in order to increase a degree of rehabilitation associated with a gait of the user. The input device may be included in a frame of the gait assistance apparatus 100, or identical functions may be performed through a remote control from an outside.

Figure 5:
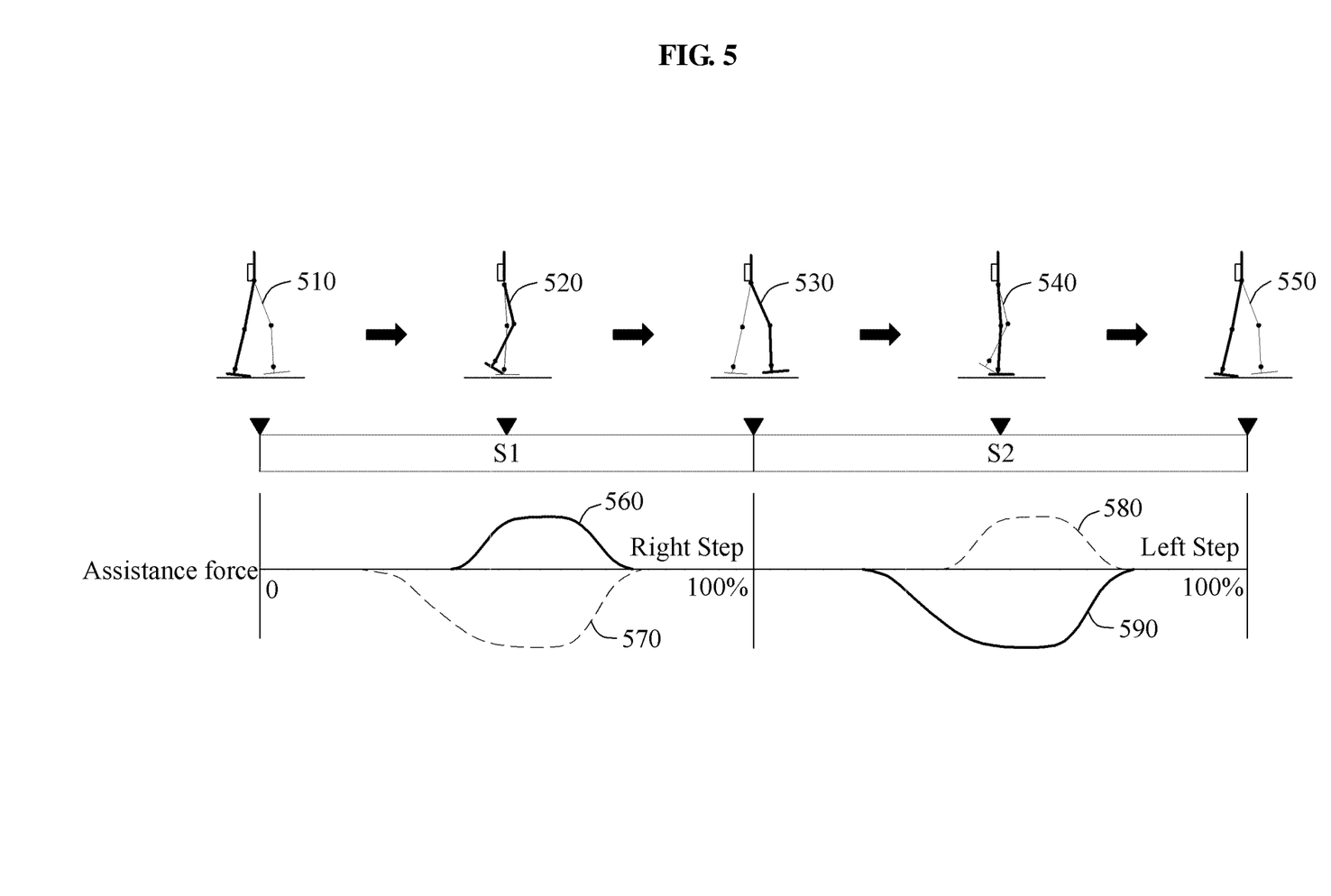
FIG. 5 is a graph illustrating a process of recognizing a gait cycle of a user using a gait assistance apparatus according to some example embodiments.

FIG. 5 is a graph illustrating a process of recognizing a gait cycle of a user using a gait assistance apparatus according to some example embodiments.

Referring to FIG. 5, in an example, the gait cycle of the user includes a right step S1 that involves a right leg swinging while a left leg acts as a pivot and a left step S2 that involves the left leg swinging while the right leg acts as the pivot.

While the user is taking the right step S1 and the left step S2, a state 510 in which a distance between both legs is greatest in response to the user pushing the left leg forward, a state 520 in which both legs of the user are parallel to each other by the right leg of the user swinging, a state 530 in which the distance between both legs is greatest in response to the user pushing the right leg forward, and a state 540 in which both legs of the user are parallel to each other by the left leg of the user swinging may occur. After the user has taken the right step S1 and the left step S2, the user may push the left leg forward such that a state 550 in which the distance between both legs is greatest in response to the user pushing the left leg forward may occur again.

The gait assistance apparatus 100 may identify the gait cycle to provide gait assistance for each step based on step motion information to be sensed. A graph of FIG. 5 represents an assistance force 560 applied to the right leg during the right step S1, an assistance force 570 applied to the left leg during the right step S1, an assistance force 580 applied to the left leg during the left step S2, and an assistance force 590 applied to the right leg during the left step S2.

Assistance forces for the right step S1 of the user also refers to the assistance force 560 applied to the right leg and the assistance force 570 applied to the left leg. When the assistance forces for the right step S1 are proportionally reflected based on a variable ratio in order to adjust assistance forces for the left step S2, the assistance force 560 applied to the right leg during the right step S1 may be used to adjust the assistance force 580 applied to the left leg during the left step S2 based on the variable ratio, and the assistance force 570 applied to the left leg during the right step S1 may be reflected to adjust the assistance force 590 applied to the right leg during the left step S2 based on the variable ratio.

Figure 6:
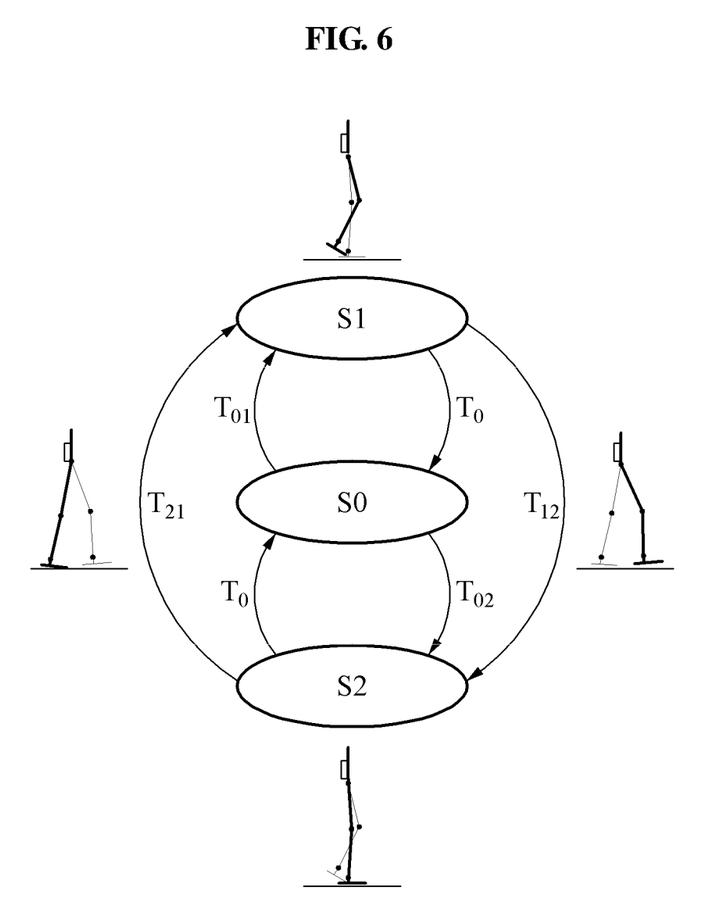
FIG. 6 is a diagram illustrating a finite state machine (FSM) used for recognizing a gait cycle of a user by a gait assistance apparatus according to some example embodiments.

FIG. 6 is a diagram illustrating a finite state machine (FSM) used for recognizing a gait cycle of a user by a gait assistance apparatus according to some example embodiments.

Referring to FIG. 6, the gait assistance apparatus 100 may recognize the gait cycle of the user using the FSM including at least one state associated with the gait cycle of the user.

For example, the FSM includes states defined as a right step S1, a left step S2, and a stop S0. The FSM determines whether transition conditions T12, T21, T01, T02, and T0 between the states S1, S2, and S0 are satisfied based on a progress of a joint angle and a joint angular velocity of the user.

In an example, the transition conditions T12, T21, $T_{01}$, $T_{02}$, and $T_0$ of the FSM may be defined as shown in Equations 1 through 5.

$$T_{12}: dq_r>0, t_{r,elap}>H_2, dq_{r,max}<H_3 \qquad \text{[Equation 1]}$$

$$T_{21}: dq_l>0, t_{l,elap}>H_2, dq_{l,max}<H_3 \qquad \text{[Equation 2]}$$

$$T_{01}: dq_l>0, q_l-q_r<H_1 \qquad \text{[Equation 3]}$$

$$T_{02}: dq_r>0, q_r-q_l<H_1 \qquad \text{[Equation 4]}$$

$$T_0: \int_{t-1}^{t} 0.5(q_r+q_l)dt - H_4 < H_5 \qquad \text{[Equation 5]}$$

In Equations 1-5, $q_r$ denotes a right hip joint angle and $q_l$ denotes a left hip joint angle, and $dq_r$ denotes a right hip joint angular velocity and $dq_l$ denotes a left hip joint angular velocity. In addition, $t_{r,elap}$ denotes an amount of time elapsed from a point in time at which the right step S1 starts and tl,elap denotes an amount of time elapsed from a point in time at which the left step S2 starts.

Thus, the gait assistance apparatus 100 may recognize the gait cycle of the user by defining a plurality of states and transition conditions and verifying whether the transition conditions are satisfied based on a progress of a joint angle and a joint angular velocity to be sensed.

Figure 7:
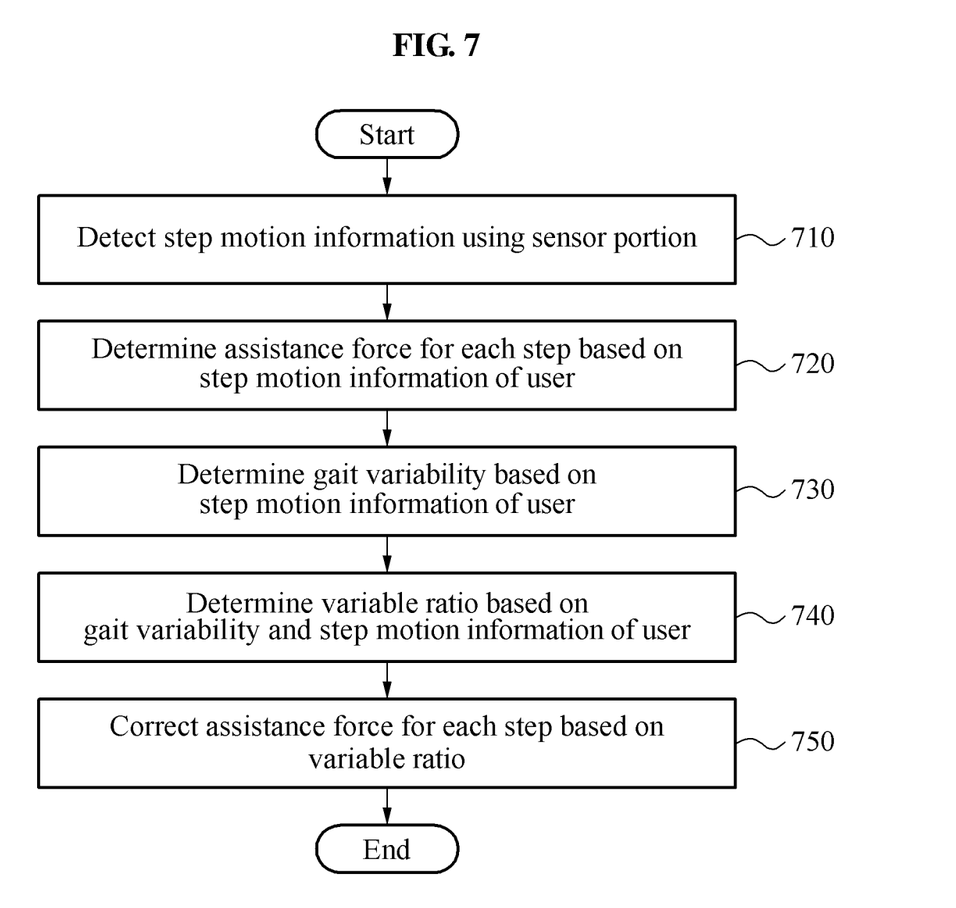
FIG. 7 is a flowchart illustrating an example of an operating method of a gait assistance apparatus according to some example embodiments.

FIG. 7 is a flowchart illustrating an example of an operating method of a gait assistance apparatus according to some example embodiments.

Referring to FIG. 7, for example, the method of FIG. 7 is used to operate the gait assistance apparatus 100 of FIG. 1.

In operation 710, the gait assistance apparatus 100 may detect step motion information of a user is detected using the sensor portion 100. The step motion information of the user may include a joint angle and a joint angular velocity associated with a step of the user, and the sensor portion 100 may include at least one of an encoder sensor and/or an inertial measurement unit (IMU) sensor to detect the step motion information.

In operation 720, the gait assistance apparatus 100 may determine an assistance force for each step based on the step motion information of the user. For example, the gait assistance apparatus 100 may determine an assistance force for a right step based on motion information of the right step, and determine an assistance force for a left step based on motion information of the left step.

In operation 730, the gait assistance apparatus 100 may determine a gait variability based on the step motion information of the user. For example, the gait assistance apparatus 100 may determine the gait variability based on a similarity between pieces of step motion information of each cycle by comparing and analyzing pieces of step motion information of each gait cycle of the user. The gait assistance apparatus 100 may use one or more of a step time, a joint motion range, a stride, a gait speed, and a bilateral symmetry as references for verifying the similarity.

In operation 740, the gait assistance apparatus 100 may determine the variable ratio based on the gait variability and the step motion information of the user. For example, the variable ratio includes a indicating a ratio of the motion information of the right step and the motion information of the left step to the assistance force for the right step and al indicating a ratio of the motion information of the left step and the motion information of the right step to the assistance force for the left step.

In operation 750, the gait assistance apparatus 100 may correct the assistance force for each step determined in operation 720. For example, the gait assistance apparatus 100 may adjust the assistance force for the right step to a value obtained by proportionally adding together a current assistance force for the right step and a current assistance force for the right step at a ratio of 1−αr:αr. The gait assistance apparatus 100 may adjust the assistance force for the left step to a value obtained by proportionally adding together the current assistance force for the left step and the current assistance force for the right step at a ratio of 1−αl:αl.

Figure 8:
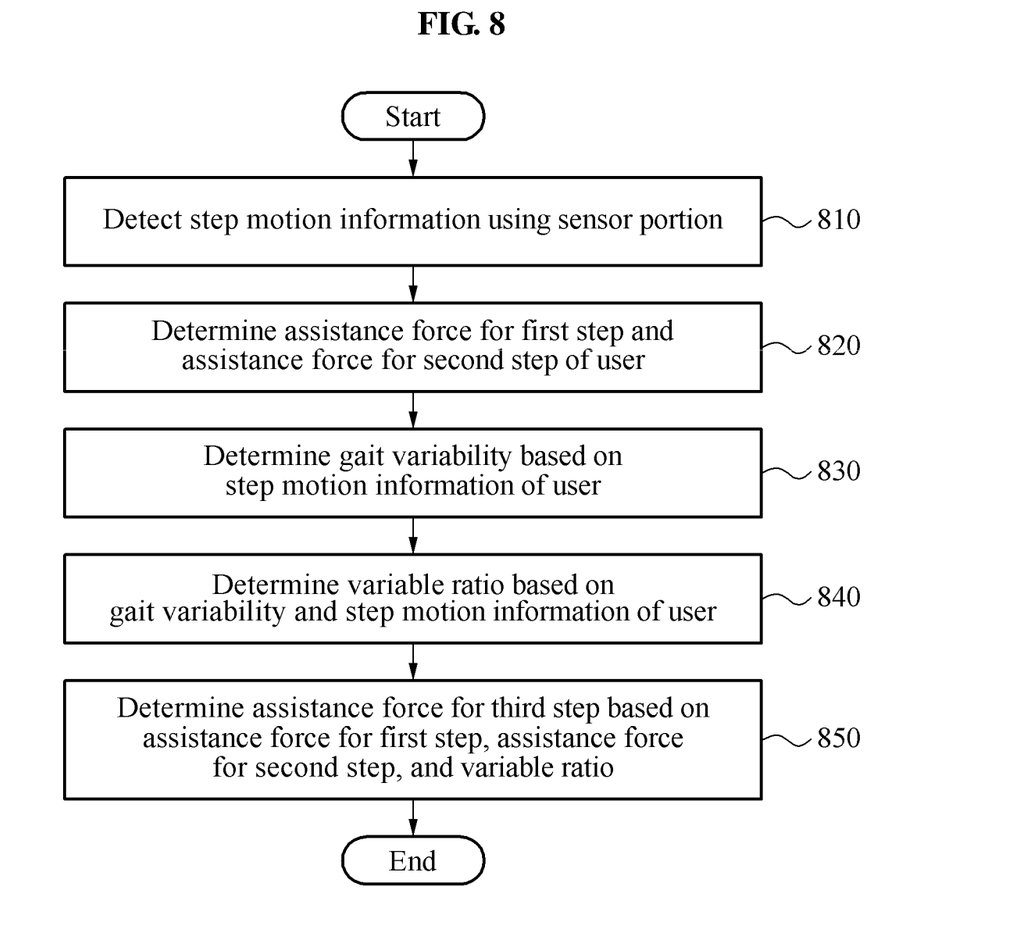
FIG. 8 is a flowchart illustrating another example of an operating method of a gait assistance apparatus according to some example embodiments.

FIG. 8 is a flowchart illustrating another example of an operating method of a gait assistance apparatus according to some example embodiments.

Referring to FIG. 8, the method of FIG. 8 may be used to operate the gait assistance apparatus 100 of FIG. 1.

In operation 810, the gait assistance apparatus 100 may detect step motion information of a user using a sensor portion. The step motion information of the user may include a joint angle and a joint angular velocity associated with a step of the user, and the sensor portion 110 may include at least one of an encoder sensor and/or an inertial measurement unit (IMU) sensor to detect the step motion information.

In operation 820, the gait assistance apparatus 100 may determine an assistance force for a first step of the user and an assistance force for a second step of the user based on the step motion information of the user. For example, in response to the first step being a right step, the second step is a left step subsequent to the first step.

In operation 830, the gait assistance apparatus 100 may determine a gait variability based on the step motion information of the user. For example, the gait assistance apparatus 100 may determine the gait variability based on a similarity between pieces of step motion information of each cycle by comparing and analyzing pieces of step motion information of each gait cycle of the user. The gait assistance apparatus 100 may use one or more of a step time, a joint motion range, a stride, a gait speed, and a bilateral symmetry as the gait assistance apparatus 100 may determine references for verifying the similarity.

In operation 840, the gait assistance apparatus 100 may determine a variable ratio based on the gait variability and the step motion information of the user. For example, the variable ratio indicates a ratio of motion information of the first step and motion information of the second step to the assistance force for the subsequent step.

In operation 850, the gait assistance apparatus 100 may determine an assistance force for a third step subsequent to the second step based on the assistance force for the first step, the assistance force for the second step, and the variable ratio. For example, in response to the first step being the right step and the second step being the left step, the third step is a right step subsequent to the second step. The gait assistance apparatus 100 may determine the assistance force for the third step] based on a value obtained by proportionally adding together the assistance force for the first step and the assistance force for the second step.

FIGS. 9 through 14 are diagrams illustrating examples of ways to implement an operating method of a gait assistance apparatus according to some example embodiments. FIGS. 9 through 14 illustrate examples of determining an assistance force for a subsequent step based on different variable ratios.

Figure 9:
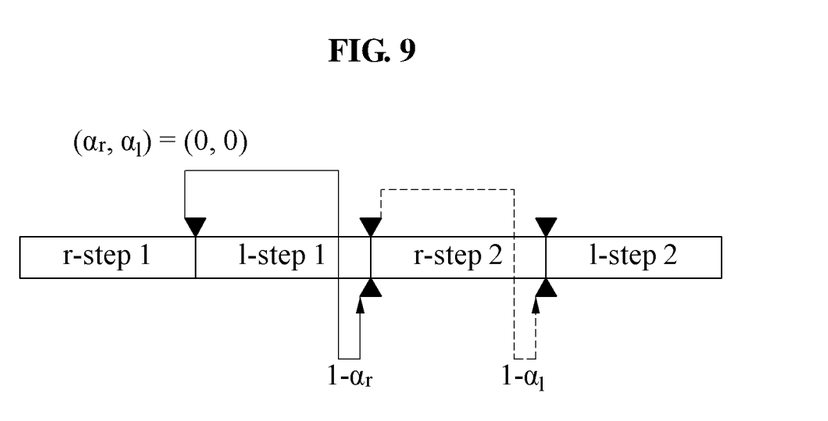
FIGS. 9 through 14 are diagrams illustrating examples of ways to implement an operating method of a gait assistance apparatus according to some example embodiments.

Referring to FIG. 9, as illustrated in FIG. 9, the gait assistance apparatus 100 may set the variable ratio to be (αr, αl)=(0, 0). In this case, an assistance force for an opposite step is not influenced by an assistance force for a step, and the left step and the right step may be individually assisted based on a natural gait style of the user.

Figure 10:
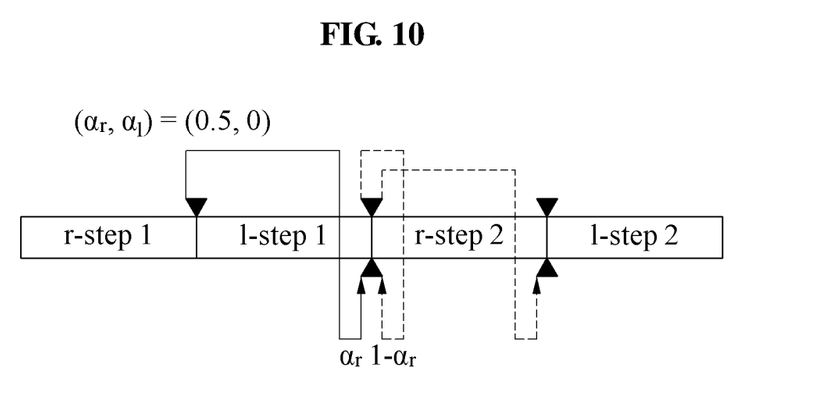

Referring to FIG. 10, as illustrated in FIG. 10, the gait assistance apparatus 100 may set the variable ratio to be (αr, αl)=(0.5, 0). In this case, the assistance force for a previous left step remains unchanged because the assistance force for the left step is not influenced by the assistance force for the right step. However, the assistance force for the previous left step influences the assistance force for the right step by a ratio of αr.

Figure 11:
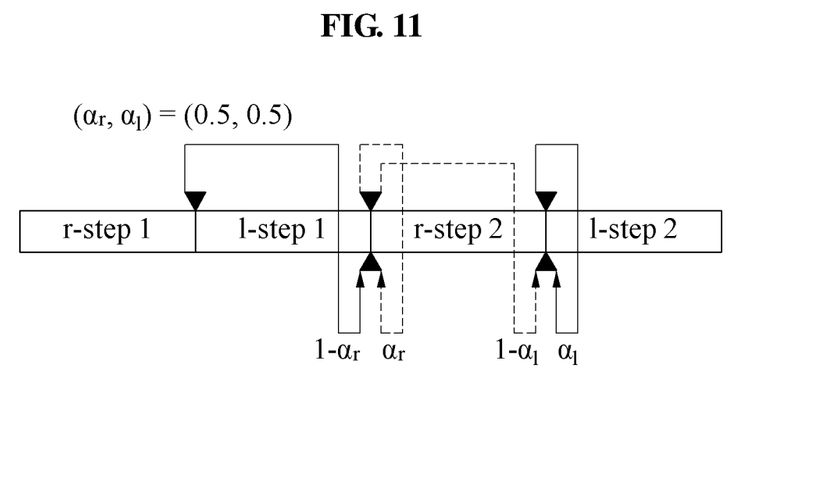

Referring to FIG. 11, as illustrated in FIG. 11, the gait assistance apparatus 100 may set the variable ratio to be (αr, αl)=(0.5, 0.5). In this case, the assistance force for the previous left step influences the assistance force for the right step by the ratio y the rationce force for the right step r the previous influences the assistance force for the left step by a ratio of f.

Figure 12:
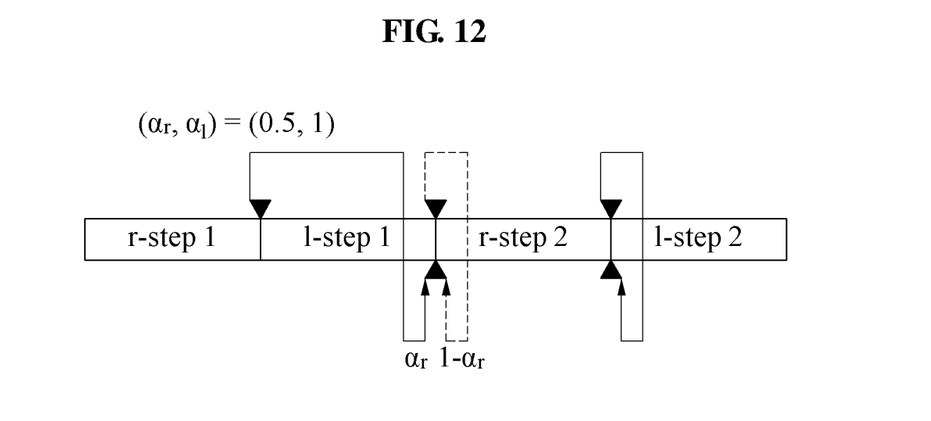

Referring to FIG. 12, as illustrated in FIG. 12, the gait assistance apparatus 100 may set the variable ratio to be ($\alpha r$, $\alpha l$)=(0.5, 1). In this case, the assistance force for the previous left step influences the assistance force for the right step by the ratio of or, and the assistance force for the left step reflects the assistance force for the previous right step which remains unchanged.

Figure 13:
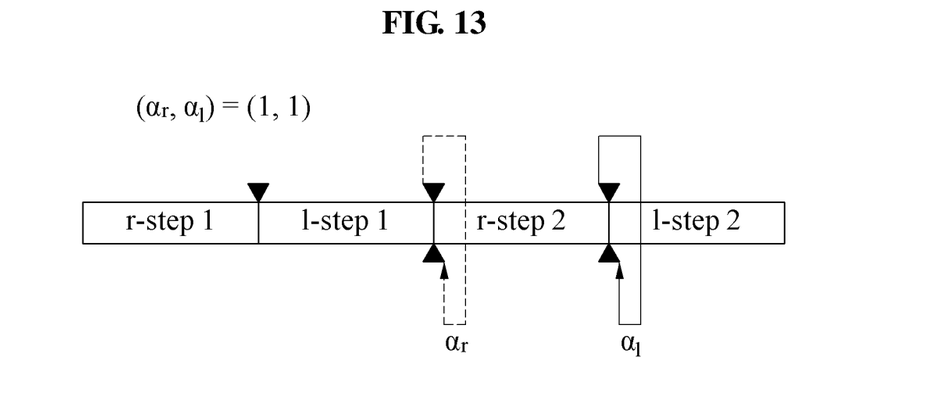

Referring to FIG. 13, as illustrated in FIG. 13, the gait assistance apparatus 100 may set the variable ratio to be ($\alpha r$, $\alpha l$)=(1, 1). In this case, the assistance force for the right step reflects the assistance force for the previous left step which remains unchanged, and the assistance force for the left step reflects the assistance force for the previous right step which remains unchanged.

Figure 14:
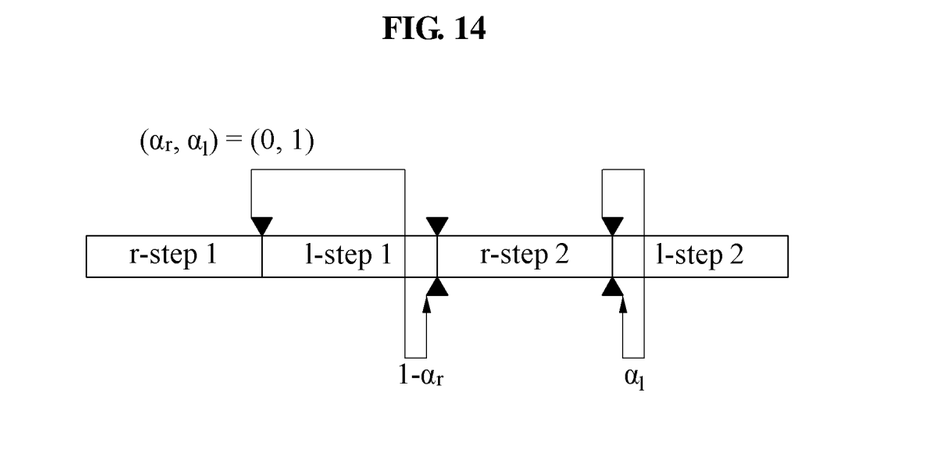

Referring to FIG. 14, as illustrated in FIG. 14, the gait assistance apparatus 100 may set the variable ratio to be ($\alpha r$, $\alpha l$)=(0, 1). In this case, because the assistance force for the right step is not influenced by the assistance force for the previous left step, the assistance force for the right step reflects the assistance force for the previous right step which remains unchanged, and the assistance force for the left step reflects the assistance force for the previous right step which remains unchanged.

The operating method of the gait assistance apparatus 100 may allow various forms of gait assistance, correction, and rehabilitation based on a set of a variable ratio as described above. A degree of correction or rehabilitation training of a gait may be gradually changed based on the proposed operating method of the gait assistance apparatus 100. In addition, an effective gait assistance strategy may be provided through various applications.

The units and/or modules described herein may be implemented using hardware components and software components. For example, the hardware components may include microphones, amplifiers, band-pass filters, audio to digital convertors, and processing devices. A processing device may be implemented using one or more hardware device configured to carry out and/or execute program code by performing arithmetical, logical, and input/output operations. The processing device(s) may include a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors.

The software may include a computer program, a piece of code, an instruction, or some combination thereof, to independently or collectively instruct and/or configure the processing device to operate as desired, thereby transforming the processing device into a special purpose processor. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. The software and data may be stored by one or more non-transitory computer readable recording mediums.

The methods according to the above-described example embodiments may be recorded in non-transitory computer-readable media including program instructions to implement various operations of the above-described example embodiments. The media may also include, alone or in combination with the program instructions, data files, data structures, and the like. The program instructions recorded on the media may be those specially designed and constructed for the purposes of example embodiments, or they may be of the kind well-known and available to those having skill in the computer software arts. Examples of non-transitory computer-readable media include magnetic media such as hard disks, floppy disks, and magnetic tape; optical media such as CD-ROM discs, DVDs, and/or Blue-ray discs; magneto-optical media such as optical discs; and hardware devices that are specially configured to store and perform program instructions, such as read-only memory (ROM), random access memory (RAM), flash memory (e.g., USB flash drives, memory cards, memory sticks, etc.), and the like. Examples of program instructions include both machine code, such as produced by a compiler, and files containing higher level code that may be executed by the computer using an interpreter. The above-described devices may be configured to act as one or more software modules in order to perform the operations of the above-described example embodiments, or vice versa.

A number of example embodiments have been described above. Nevertheless, it should be understood that various modifications may be made to these example embodiments. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. A method of operating a gait assistance apparatus, the method comprising:
sensing, using a sensor, step motion information during at least a prior gait cycle of a user;
determining, by at least one processor, a first assistance force and a second assistance force to be applied by the gait assistance apparatus to the user for assisting respective ones of a right step of a right leg of the user and a left step of a left leg of the user in a current gait cycle based on the step motion information, the current gait cycle being subsequent to the prior gait cycle;
determining, by the at least one processor, a variable ratio based on the step motion information of the user, the variable ratio being a ratio of a first variable to a second variable, the first variable indicating an amount the second assistance force for assisting the left step of the user during the prior gait cycle influences the first assistance force for assisting the right step of the user during the current gait cycle, and the second variable indicating an amount the first assistance force for assisting the right step of the user during the prior gait cycle influences the second assistance force for assisting the left step of the user during the current gait cycle;

adjusting, by the at least one processor, the first assistance force and the second assistance force based on the variable ratio to generate an adjusted first assistance force and an adjusted second assistance force for assisting respective ones of the right step and the left step of the user in the current gait cycle; and instructing, by the at least one processor, a driver to transmit the adjusted first assistance force to the right leg of the user during the current gait cycle and the adjusted second assistance force to the left leg of the user during the current gait cycle.

2. The method of claim 1, wherein the determining the variable ratio comprises:

determining a gait variability of the user based on the step motion information of the user; and determining the variable ratio based on the gait variability and a reference value.

3. The method of claim 2, wherein the determining of the gait variability comprises:

identifying the current gait cycle of the user, based on the step motion information of the user; and determining the gait variability based on a similarity between the step motion information obtained during the current gait cycle and the step motion information obtained during the prior gait cycle.

4. The method of claim 3, further comprising:

determining the similarity between the step motion information obtained during the current gait cycle and the step motion information obtained during the prior gait cycle by comparing (i) one or more of a step time, a joint motion range, a stride, a gait speed and a bilateral symmetry associated with the current gait cycle and (ii) one or more of the step time, the joint motion range, the stride, the gait speed and the bilateral symmetry associated with the prior gait cycle.

5. The method of claim 2, wherein the determining the variable ratio based on the gait variability and the reference value comprises:

increasing, by the at least one processor, the variable ratio in response to the gait variability being less than the reference value such that the amount the second assistance force for assisting the left step of the user during the prior gait cycle influences the first assistance force for assisting the right step of the user during the current gait cycle increases and the amount the first assistance force for assisting the right step of the user during the prior gait cycle influences the second assistance force for assisting the left step of the user during the current gait cycle increases; and decreasing, by the at least one processor, the variable ratio in response to the gait variability being greater than or equal to the reference value such that the amount the second assistance force for assisting the left step of the user during the prior gait cycle influences the first assistance force for assisting the right step of the user during the current gait cycle decreases and the amount the first assistance force for assisting the right step of the user during the prior gait cycle influences the second assistance force for assisting the left step of the user during the current gait cycle decreases.

6. The method of claim 1, wherein the determining, by at least one processor, the first assistance force and the second assistance force comprises:

determining the first assistance force sufficient to swing the right leg of the user while the left leg of the user acts as a pivot, and determining the second assistance force sufficient to swing the left leg of the user while the right leg of the user acts as the pivot.

7. A gait assistance apparatus comprising:

at least one sensor configured to sense step motion information during at least a prior gait cycle of a user; and a processor configured to:

determine a first assistance force and a second assistance force to be applied by the gait assistance apparatus to the user for assisting respective ones of a right step of a right leg of the user and a left step of a left leg of the user in a current gait cycle based on the step motion information, the current gait cycle being subsequent to the prior gait cycle, determine a variable ratio based on the step motion information of the user, the variable ratio being a ratio of a first variable to a second variable, the first variable indicating an amount the second assistance force for assisting the left step of the user during the prior gait cycle influences the first assistance force for assisting the right step of the user during the current gait cycle, and the second variable indicating an amount the first assistance force for assisting the right step of the user during the prior gait cycle influences the second assistance force for assisting the left step of the user during the current gait cycle adjust the first assistance force and the second assistance force based on the variable ratio to generate an adjusted first assistance force and an adjusted second assistance force for assisting respective ones of the right step and the left step of the user in the current gait cycle, and instructing a driver to transmit the adjusted first assistance force to the right leg of the user during the current gait cycle and the adjusted second assistance force to the left leg of the user during the current gait cycle.

8. The gait assistance apparatus of claim 7, wherein the processor is configured to:

determine a gait variability of the user based on the step motion information of the user, and determine the variable ratio based on the gait variability and a reference value.

9. The gait assistance apparatus of claim 8, wherein the processor is configured to:

identify the current gait cycle of the user, based on the step motion information of the user, and determine the gait variability based on a similarity between the step motion information obtained during the current gait cycle and the step motion information obtained during the prior gait cycle.

10. The gait assistance apparatus of claim 9, wherein the processor is configured to, determine the similarity between the step motion information obtained during the current gait cycle and the step motion information obtained during the prior gait cycle by comparing (i) one or more of a step time, a joint motion range, a stride, a gait speed and a bilateral symmetry associated with the current gait cycle and (ii) one or more of the step time, the joint motion range, the stride, the gait speed and the bilateral symmetry associated with the prior gait cycle.

11. The gait assistance apparatus of claim 8, wherein the processor is configured to determine the variable ratio by,
- increasing the variable ratio in response to the gait variability being less than the reference value such that the amount the second assistance force for assisting the left step of the user during the prior gait cycle influences the first assistance force for assisting the right step of the user during the current gait cycle increases and the amount the first assistance force for assisting the right step of the user during the prior gait cycle influences the second assistance force for assisting the left step of the user during the current gait cycle increases, and
- decreasing the variable ratio in response to the gait variability being greater than or equal to the reference value such that the amount the second assistance force for assisting the left step of the user during the prior gait cycle influences the first assistance force for assisting the right step of the user during the current gait cycle decreases and the amount the first assistance force for assisting the right step of the user during the prior gait cycle influences the second assistance force for assisting the left step of the user during the current gait cycle decreases.

12. The gait assistance apparatus of claim 7, wherein the processor is configured to:
- determine the first assistance force sufficient to swing the right leg of the user while the left leg of the user acts as a pivot, and
- determine the second assistance force sufficient to swing the left leg of the user while the right leg of the user acts as the pivot.

* * * * *